United States Patent [19]

Akram et al.

[11] Patent Number: 5,163,970
[45] Date of Patent: Nov. 17, 1992

[54] NITRO-P-PHENYLENEDIAMINE DERIVATIVES, PROCESSES FOR THEIR PREPARATION AND COLORING AGENTS CONTAINING THESE FOR USE ON KERATIN FIBRES

[75] Inventors: Mustafa Akram, Offenbach; Winfried Seidel, Ellerbek, both of Fed. Rep. of Germany

[73] Assignee: Hans Schwarzkopf GmbH, Hamburg, Fed. Rep. of Germany

[21] Appl. No.: 746,415

[22] Filed: Aug. 16, 1991

Related U.S. Application Data

[63] Continuation-in-part of Ser. No. 513,996, Apr. 25, 1990, Pat. No. 5,067,967.

[30] Foreign Application Priority Data

May 26, 1989 [DE] Fed. Rep. of Germany ....... 3917114

[51] Int. Cl.$^5$ .............................................. A61K 7/13
[52] U.S. Cl. ................................... 8/415; 8/407; 8/408; 8/416; 8/429; 564/441; 564/442
[58] Field of Search ................... 564/441, 442; 8/407, 8/408, 415, 416, 429

[56] References Cited

U.S. PATENT DOCUMENTS

| | | | |
|---|---|---|---|
| 3,973,900 | 8/1976 | Husemeyer | 8/407 |
| 4,704,474 | 11/1987 | Konrad | 8/407 |
| 4,725,283 | 2/1988 | Cotteret | 8/429 |
| 5,067,967 | 11/1991 | Akram | 8/415 |
| 5,091,581 | 2/1992 | Seidel | 564/441 |

Primary Examiner—Jack Cooper
Assistant Examiner—Thomas Steinberg
Attorney, Agent, or Firm—Beveridge, DeGrandi & Weilacher

[57] ABSTRACT

Compounds of the formula I are described:

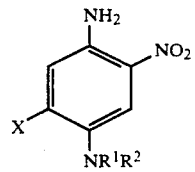

wherein $R^1$ and $R^2$ independently of one another each represent a hydrogen atom, a ($C_1$–$C_2$) alkyl group, a hydroxy ($C_2$–$C_3$) alkyl group or a 2,3-dihydroxypropyl group and X is a fluorine atom, with the proviso that when $R^1$ or $R^2$ is hydrogen then the other is not a hydroxy ($C_2$) alkyl group; processes for their preparation and aqueous hair coloring agents containing these compounds.

10 Claims, 8 Drawing Sheets

NITRO-P-PHENYLENEDIAMINE DERIVATIVES, PROCESSES FOR THEIR PREPARATION AND COLORING AGENTS CONTAINING THESE FOR USE ON KERATIN FIBRES

REFERENCE TO RELATED APPLICATIONS

This application is a continuation-in-part of our co-pending U.S. patent application Ser. No. 07/513,996, Apr. 25, 1990 U.S. Pat. No. 5,067,967 which is relied on and incorporated by reference.

INTRODUCTION TO THE INVENTION

The present invention relates to new nitro-p-phenylenediamine derivatives, processes for their preparation and colouring agents which contain these for use on keratin fibres.

Nitro dyestuffs play an important role in hair colouring. They have found wide use both in direct colouring and in oxidation colouring. These dyestuffs must primarily meet the following technological requirements: During colouring, they must produce the desired colour with an adequate intensity. The colours achieved should have a good fastness to light and acid and should not tend towards shifts in the colour of the original shade under wearing conditions. They should moreover be toxicologically and dermatologically acceptable.

Nitro-p-phenylenediamine derivatives in which the amino group in the 4-position can be mono- or disubstituted and in which the aromatic nucleus is optionally substituted in the other positions have already been proposed as red directly absorbing hair dyestuffs or as an additive during oxidation colouring. $N^4$-Substituted 5-chloro-1,4-diamino-2-nitrobenzenes which are said to colour the hair in the red range are described in DE-AS 2,157,844 and in DE-OS 3,323,207. However, these dyestuffs have some disadvantages. The solubility, which plays an important role for perfect colouring, is very low in the case of these dyestuffs. The luminosity and the colour intensity of the colours achieved are also not satisfactory.

SUMMARY OF THE INVENTION

An object of the present invention is to provide new compounds, processes for their preparation, and aqueous hair colouring agents which can be used as directly absorbing dyestuffs in the red range, have a good solubility and produce an intensive coloration of suitable luminosity. This object is achieved by the compounds of the general formula I

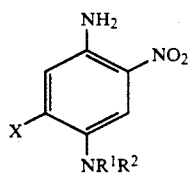

wherein $R^1$ and $R^2$ independently of one another each represent a hydrogen atom, a ($C_1$-$C_2$) alkyl group, a hydroxy ($C_2$-$C_3$) alkyl group or a 2,3-dihydroxypropyl group and X represents a fluorine atom, with the proviso that when $R^1$ and $R^2$ is hydrogen then the other is not a hydroxy ($C_2$) alkyl group.

In addition to the compounds of the general formula I as above described, the invention also relates to processes for their preparation and aqueous hair colouring agents containing same.

DETAILED DESCRIPTION OF THE INVENTION

Figure 1:
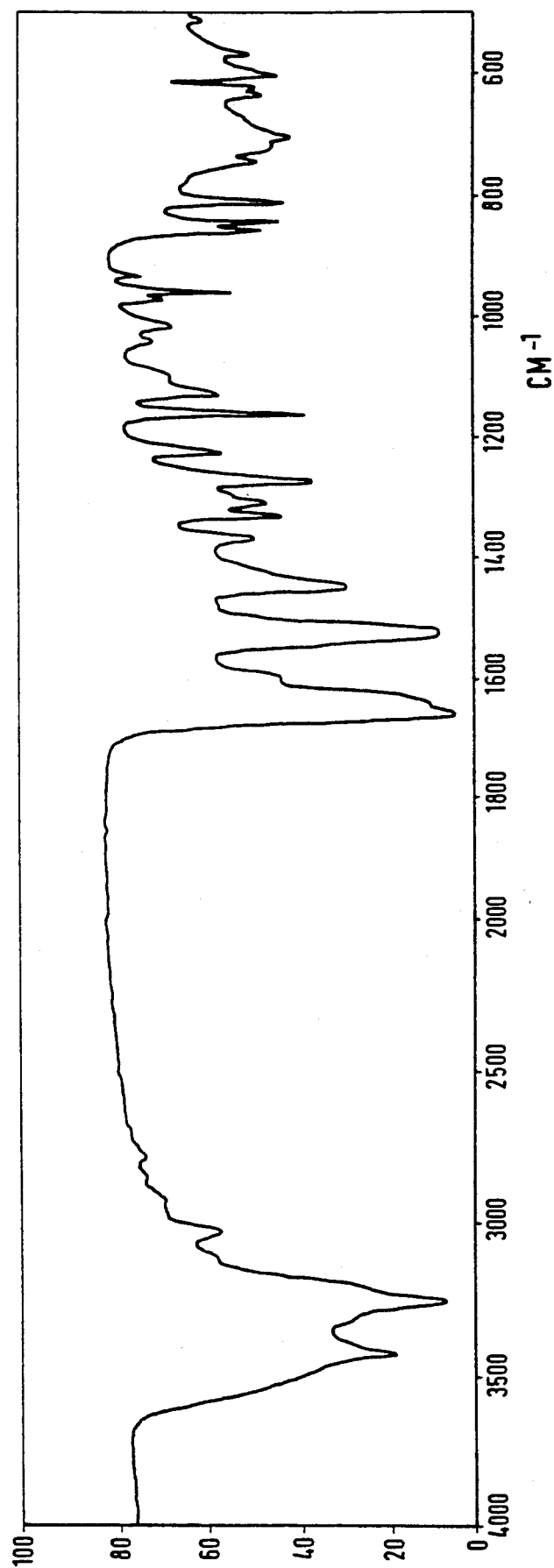
FIG. 1 shows the IR spectrum of 1-amino-4-acetylamino-3-fluorobenzene.

Details of the processes according to the invention are described below.

The bisacetyl compounds of the general formula II

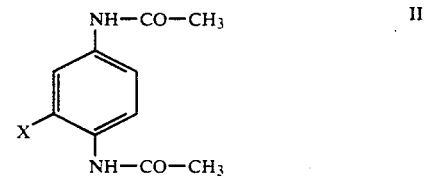

wherein X is F, can be obtained by reaction of the compounds of the general formula III

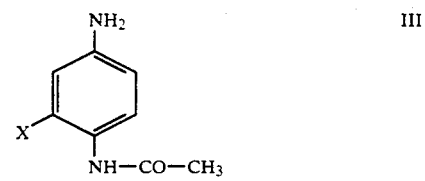

wherein X has the same meaning, with acetic anhydride (compare S. Sugawara and N. Ishikawa, J. Chem. Soc. Japan, Ind. Chem. Sect. (Kogyo Kagaku Zasshi) 72 (1969), 11, 2425-2429).

The compounds of the formula III are obtained by reduction of the compounds of the general formula IV

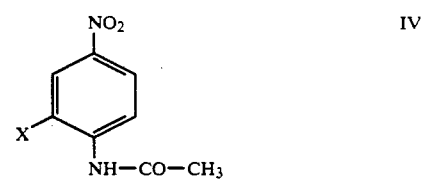

wherein X is F, with base metals or by catalytic reductions (compare Nobuo Ishikawa, Toschio Tanabe, Kogyo Kagaku Zasshi, 70 (9), 1530-2; Leif Grehn, Kerstin Gunnarson, Ulf Rognarsson, Acta Chem. Scand., Ser. B, B 40 (9), 745-50 and F. Bruce Cain, J. Graham Atwell, A. William Denny, J. Med. Chem., 18

(11), 1110–17). The nitration of the bisacetyl compounds of the general formula II can be carried out in glacial acetic acid or in sulfuric acid, it being possible to use a nitric acid/glacial acetic acid or nitric acid-sulfuric acid mixture in a ratio of 1/1 to ⅓ or in a ratio of 1/5 to 1/10 respectively as the nitrating mixture. Heating of the nitro compounds of the formula III (X is F) with a strong inorganic acid in an aqueous medium gives the free amino compounds of the formula I, wherein $R^1$ and $R^2$ are hydrogen atoms and X is F. Monoalkylation of these diamino compounds of the general formula I ($R^1$ and $R^2$ are hydrogen atoms and X denotes F) can be achieved by reaction with an alkylating agent (for example dimethyl sulphate or diethyl sulphate). The reaction can be carried out in water at a temperature of 40° C. to 90° C., preferably at 60° C., the addition of up to about 30% of a water-miscible inert solvent (for example monoethylene glycol dimethyl ether) accelerating this. A pH-controlled reaction in which an alkylating agent and an alkali (for example sodium hydroxide solution) are simultaneously added to the nitro-p-phenylenediamine derivatives in the course of one hour is advantageous.

To prepare the compounds of the general formula I, wherein $R^1$ and $R^2$ have the meaning $CH_2CH_2OH$ and X is F, first the compounds of the formula I, wherein $R^1$ and $R^2$ are hydrogen atoms and X is F, can be reacted with ethylene oxide, ethylene oxide being passed in portions into a suspension or solution of the free amino compound in water or in an inert organic solvent (for example monoethylene glycol dimethyl ether or dioxane) at a temperature of 40° C. to 80° C., preferably at 60° C., in the course of 90 minutes. The reaction is monitored by thin layer chromatography and can be ended promptly after the monohydroxyalkylation, and the product is isolated and purified by recrystallization. The introduction of another hydroxyethyl group is achieved by passing further ethylene oxide into a suspension or solution of the monohydroxyalkyl compound in water or in an inert organic solvent (for example monoethylene glycol dimethyl ether or dioxane) at about 60° C. The reaction is likewise monitored by thin layer chromatography and is interrupted promptly after the $N^4$, $N^4$-dihydroxyethylation. The time over which ethylene oxide is passed in is about 75 minutes. After cooling, the product is isolated and purified by the $N^1,N^4,N^4$-trihydroxyethyl product, formed as a by-product, by recrystallization or column chromatography. The compounds of the formula I, wherein $R^1$ and $R^2$ have the meaning $CH_2CH_2OH$ and X is F, are obtainable in this way.

To introduce a hydroxypropyl or 2,3-dihydroxy-propyl group, the free amino compounds of the formula I ($R^1$ and $R^2$ are hydrogen atoms and X if F) are reacted with a hydroxypropyl halide or with a 2,3-dihydroxypropyl halide. The reaction is carried out, for example, in dimethylformamide, in monoethylene glycol dimethyl or in dioxane at a temperature of 75° C. to 95° C. in the presence of an acid-trapping agent (for example sodium acetate or triethylamine). The reaction time is about 12 hours. The monoalkylated and monohydroxyalkylated compounds can be converted by further reaction with alkylating agents which contain the radicals ($C_1$–$C_2$) alkyl, hydroxy, ($C_2$–$C_3$) alkyl of 2,3-dihydroxy-propyl into the compounds of the formula I, wherein $R^1$ and $R^2$ independently of one another each represent a ($C_1$–$C_2$) alkyl group, a hydroxy ($C_2$–$C_3$) alkyl group or a 2,3-dihydroxypropyl group and X represents a fluorine atom.

The reaction can likewise be carried out in one of the abovementioned solvents at a temperature of 70° C. and 90° C. Triethylamine, for example, can be used as the acid-trapping agent. The reaction time is about 16 hours. The $N^4,N^4$-dialkyl product is then purified by recrystallization or by column chromatography. The hydroxyethylation of the monoalkylated compounds can also be carried out by reaction with ethylene oxide. For this, ethylene oxide is passed in portions into a suspension or solution of the monoalkyl compound in water or in an inert organic solvent (for example monoethylene glycol) dimethyl ether or dioxane) at a temperature of about 60° C. in the course of one hour. After cooling, the product which has precipitated is filtered off and purified by crystallization or by column chromatography.

The preparation processes are illustrated by the following examples.

EXAMPLES

Example 1

Preparation of 1,4-diamino-5-fluoro-2-nitrobenzene

A. Preparation of 1-amino-4-acetylamino-3-fluorobenzene 198 g (1 mol) of 1-acetylamino-2-fluoro-4-nitrobenzene are transferred into a stainless steel autoclave together with 510 ml of methanol, about 3 g of palladium-on-charcoal (5%) are added and catalytic reduction is carried out in the course of 4 hours at 50° C. under a hydrogen pressure of 15 bar. After the catalyst has been removed, 450 ml of methanol are distilled off from the reaction solution in vacuo, the product which has precipitated is filtered off with suction and the residue is washed with a little methanol and dried at 50°–60° C. in a vacuum cabinet.

Yield: 147 g (87.5% of the theoretical value).
Melting point: 135° C.
IR spectrum: see FIG. 1.

B. Preparation of 1,4-bisacetylamino-2-fluorobenzene 134.5 g (0.8 mol) of the 1-amino-4-acetylamino-3-fluorobenzene prepared above under A. are heated at 85° C. together with 800 ml of water and 34 g of acetic acid. 86.5 g of acetic anhydride are added to this mixture in the course of one hour. The reaction mixture is subsequently stirred at the same temperature for a further hour and cooled to 15° C. The product which has precipitated is then filtered off, washed twice with 150 ml of water each time and dried.

Figure 2:
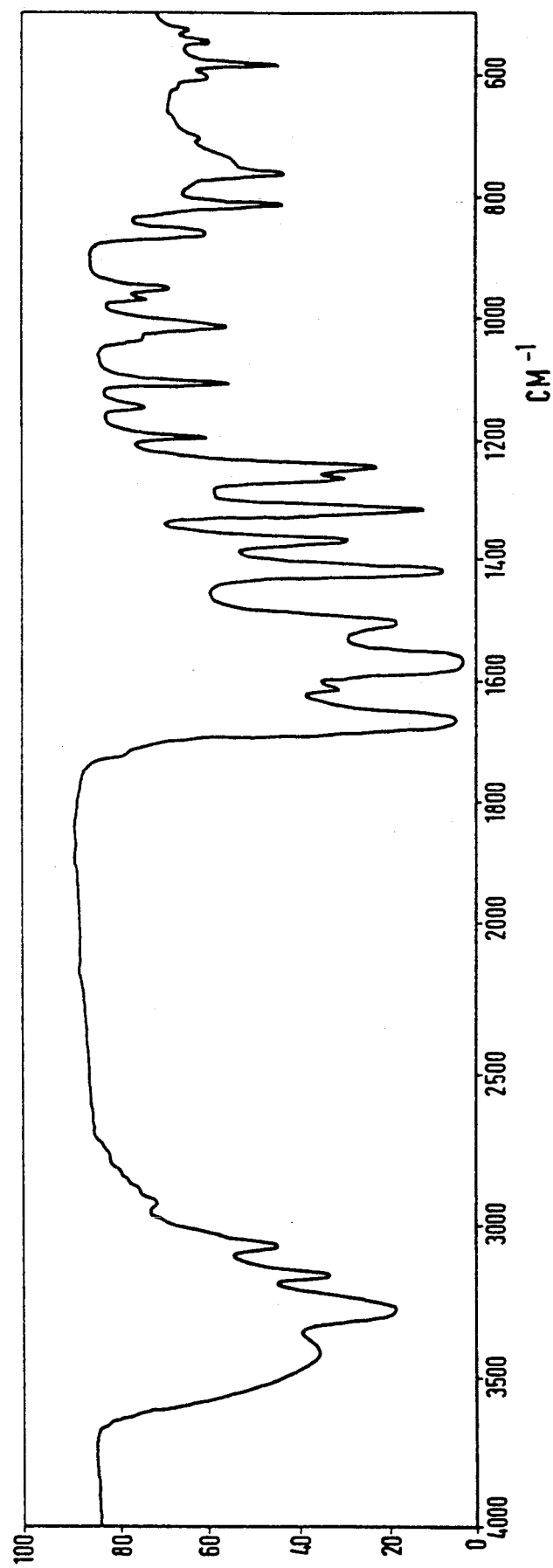
FIG. 2 shows the IR spectrum of 1,4-bisacetylamino-2-fluorobenzene.

Yield: 163 g (97% of the theoretical value).
Melting point: above 225° C.
IR spectrum: see FIG. 2.

C. Preparation of 1,4-bisacetylamino-2-fluoro-5-nitrobenzene 157.5 g (0.75 mol) of the 1,4-bisacetylamino-2-fluorobenzene obtained above under B. are initially introduced into 630 g of glacial acetic acid, and a mixture of 42 g of glacial acetic acid and 51 g of nitric acid (density 1.5) is added dropwise in the course of 2 hours. The mixture is subsequently stirred at 40° C. for a further 2 hours and cooled to 15° C. After the product which has precipitated has been filtered off, it is washed twice with 50 ml of glacial acetic acid each time and dried at 50° C. in a vacuum cabinet.

Figure 3:
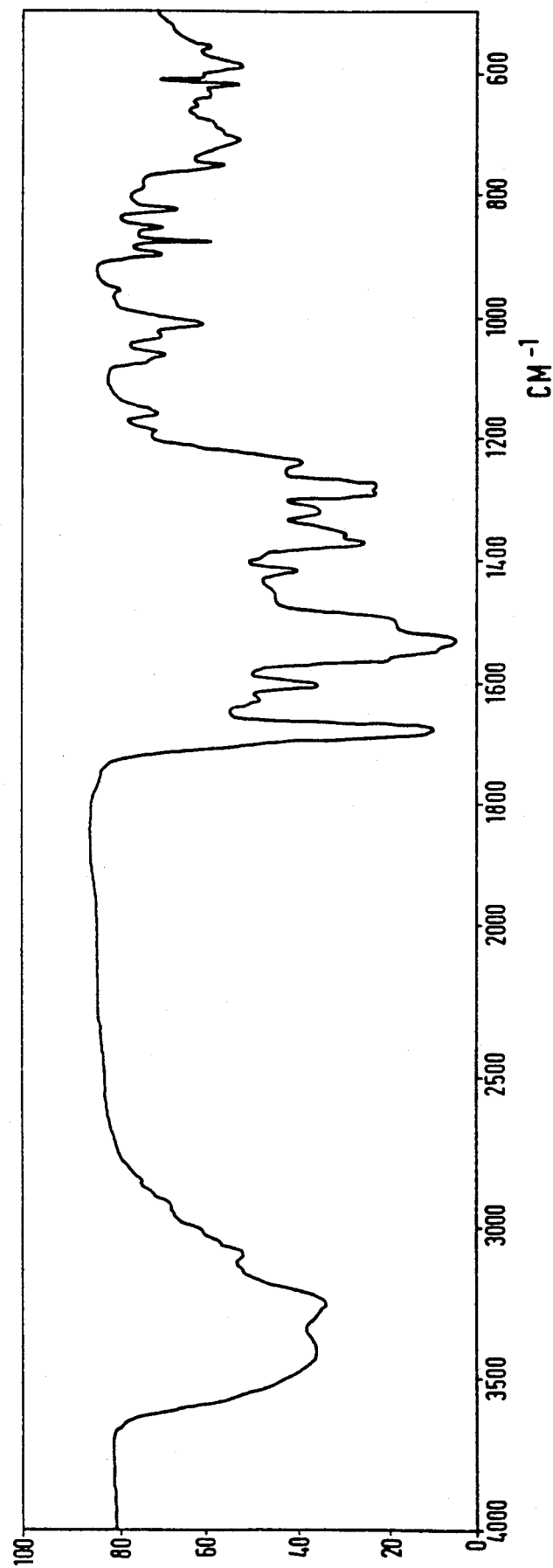
FIG. 3 shows the IR spectrum of 1,4-bisacetylamino-2-fluoro-5-nitrobenzene.

Yield: 166.5 g (87% of the theoretical value).
Melting point: 215° C.
IR spectrum: see FIG. 3.

D. Preparation of 1,4-diamino-5-fluoro-2-nitrobenzene 166 g (0.65 mol) of the 1,4-bisacetylamino-2-fluoro-5-nitrobenzene prepared according to C. are heated at 98° C. together with 812 ml of water and 240 g of concentrated hydrochloric acid (36% strength), and the reaction mixture is stirred at this temperature for one hour. The mixture is then first cooled to 60° C., the pH is brought to 7.5 with 25% strength aqueous ammonia solution and the mixture is further cooled to 5° C. The product is now filtered off, washed twice with 75 ml of water each time and dried.

Figure 4:
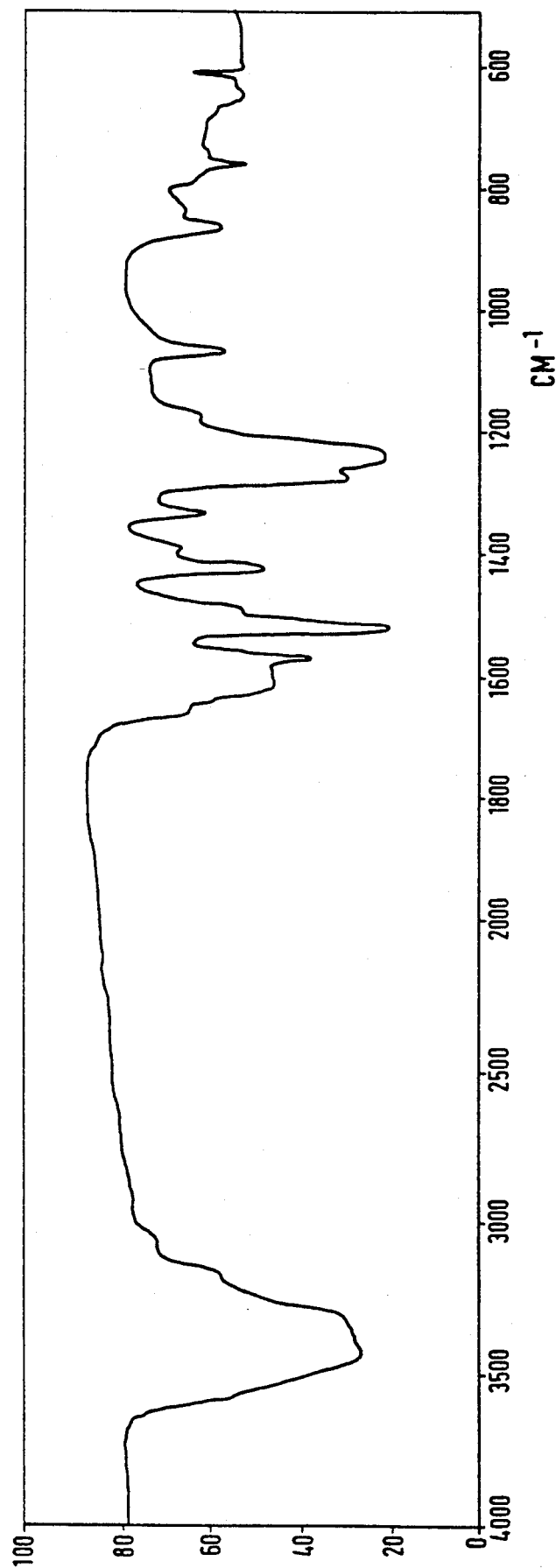
FIG. 4 shows the IR spectrum of 1,4-diamino-5-fluoro-2-nitrobenzene.

Yield: 106 g (95% of the theoretical value)
Melting point: 139° C.
IR spectrum: see FIG. 4.

Example 2

Preparation of 1-amino-4-(2,3-dihydroxypropylamino)-5-fluoro-2-nitrobenzene 3.4 (0.02 mol) of 1,4-diamino-5-fluoro-2-nitrobenzene are heated at 95° C. together with 6.6 g of chloro-2,3-propanediol and 10 ml of dimethylformamide, 2 g of sodium acetate are added to this mixture and the temperature is kept at 95° C. for 12 hours. 40 ml of water are then added and the reaction solution is extracted with ethyl acetate. 4.8 g of oil are obtained after the solvent has been distilled off.

1.2 g of pure 1-amino-4-(2,3-dihydroxypropylamino)-5-fluoro-2-nitrobenzene are obtained by column chromatography.

Figure 6:
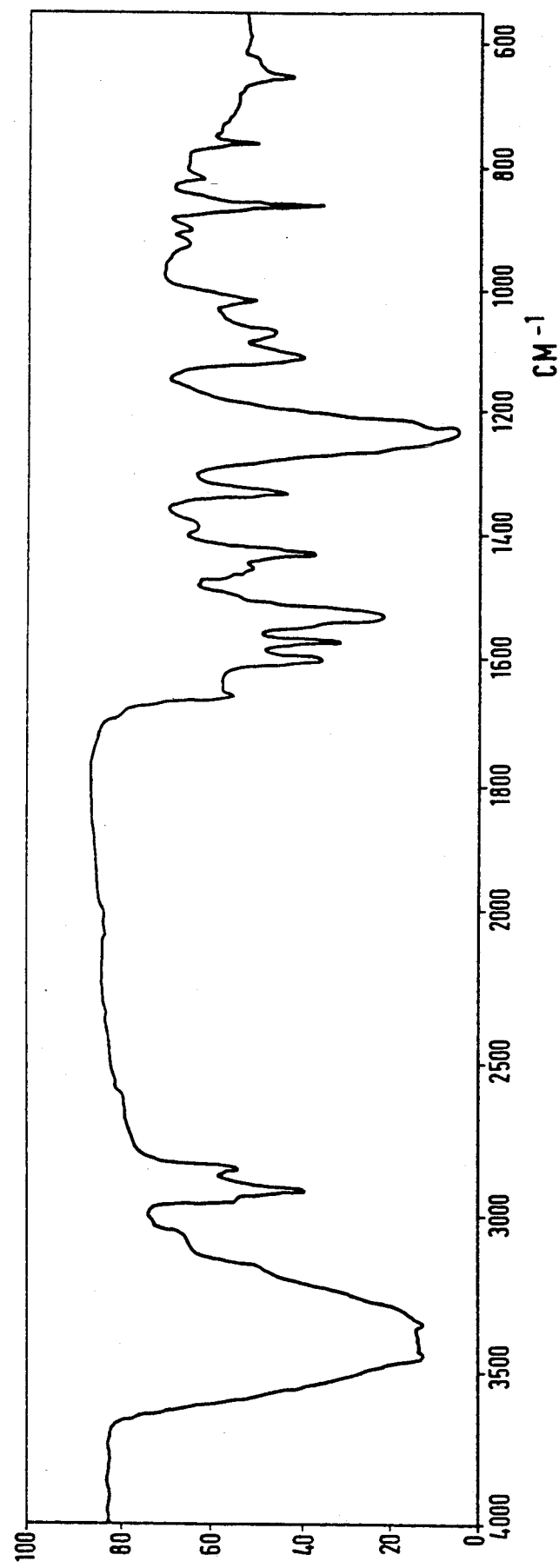
FIG. 6 shows the IR spectrum of 1-amino-4-(2,3-dihydroxypropylamino)-5-fluoro-2-nitrobenzene.

Yield: 1.2 g (24% of theoretical value).
Melting point: 129°-130° C.
IR spectrum: see FIG. 6.
$^1$H—NMR spectrum: (DMSO-$d_6$) $\delta = 2.6-3.1$ (2H, $CH_2$—N); $\delta = 3.2-3.8$ (3H, $CH_2O$, CH—O); $\delta = 6.6-7.5$ (m, 2H, Ar—H).

Example 3

Preparation of 1-amino-5-fluoro-4-methylamino-2-nitrobenzene 8.6 g (0.05 mol) of 1,4-diamino-5-fluoro-2-nitrobenzene are initially introduced into a mixture of 35 ml of water and 20 g of monoethylene glycol dimethylether. 9.75 g of dimethyl sulphate and 5% strength sodium hydroxide solution are simultaneously added dropwise at 60° C. so that the pH of the reaction mixture remains between 7.5 and 8.5. The addition time for the dimethylsulphate and sodium hydroxide solution is about 60 minutes. The mixture is then subsequently stirred at 60° C. for one hour, and when the reaction has ended the solvent is distilled off, the residue is cooled at 10° C. and the product which has precipitated is filtered off with suction.

Recrystallization twice from ethanol gives 3.7 g of 1-amino-5-fluoro-4-methylamino-2-nitrobenzene.

Figure 7:
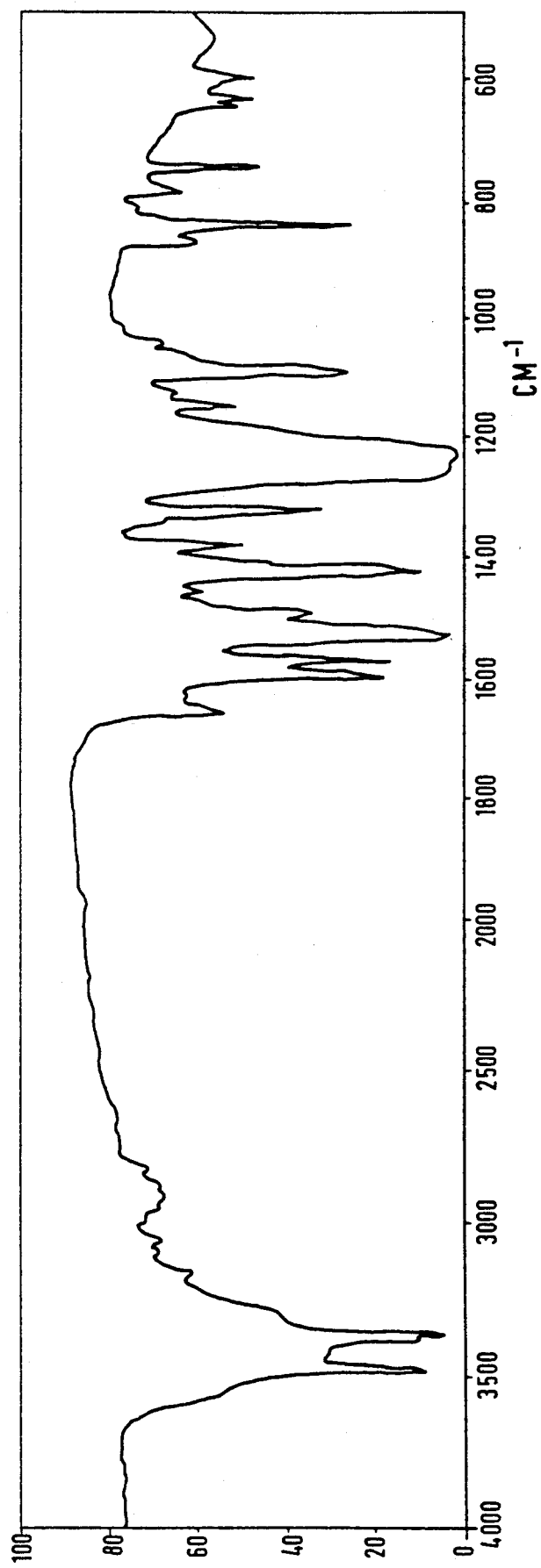
FIG. 7 shows the IR spectrum of 1-amino-5-fluoro-4-methylamino-2-nitrobenzene.

Yield: 3.7 g (40% of the theoretical value).
Melting point: 176° C.
IR Spectrum: see FIG. 7.
$^1$—NMR spectrum: (DMSO-$d_6$) $\delta = 2.7$ (3H, $CH_3$—N); $\delta = 5.4$ (1H, N—H); $\delta = 6.8-7.1$ (4H, Ar—H); $\delta = 7.25$ (2H, $NH_2$).

Example 4

Preparation of 1-amino-4-di(2-hydroxyethylamino)-5-fluoro-2-nitrobenzene

Ethylene oxide is passed in portions into a mixture of 8.6 g (0.05 mol) of 1,4-diamino-5-fluoro-2-nitrobenzene, 50 ml of water and 5 g of monoethylene glycol dimethyl ether at 60° C. and the reaction is monitored by thin layer chromatography. The monohydroxyethylated product is first formed. The monohydroxyethyl compound is converted into a mixture of 1-amino-4-di(2-hydroxyethylamino)-5-fluoro-2-nitrobenzene and 1-(2-hydroxyethylamino)-4-di-(2-hydroxyethylamino)-5-fluoro-2-nitrobenzene by passing in further ethylene oxide. The ethylene oxide is passed into the mixture in portions, this taking about 75 minutes. After cooling, the reaction mixture is extracted with ethyl acetate, the solvent is distilled off and the resulting oil is separated by column chromatography. 4.2 of pure 1-amino-4-di(2-hydroxyethylamino)-5-fluoro-2-nitrobenzene are obtained.

Figure 8:
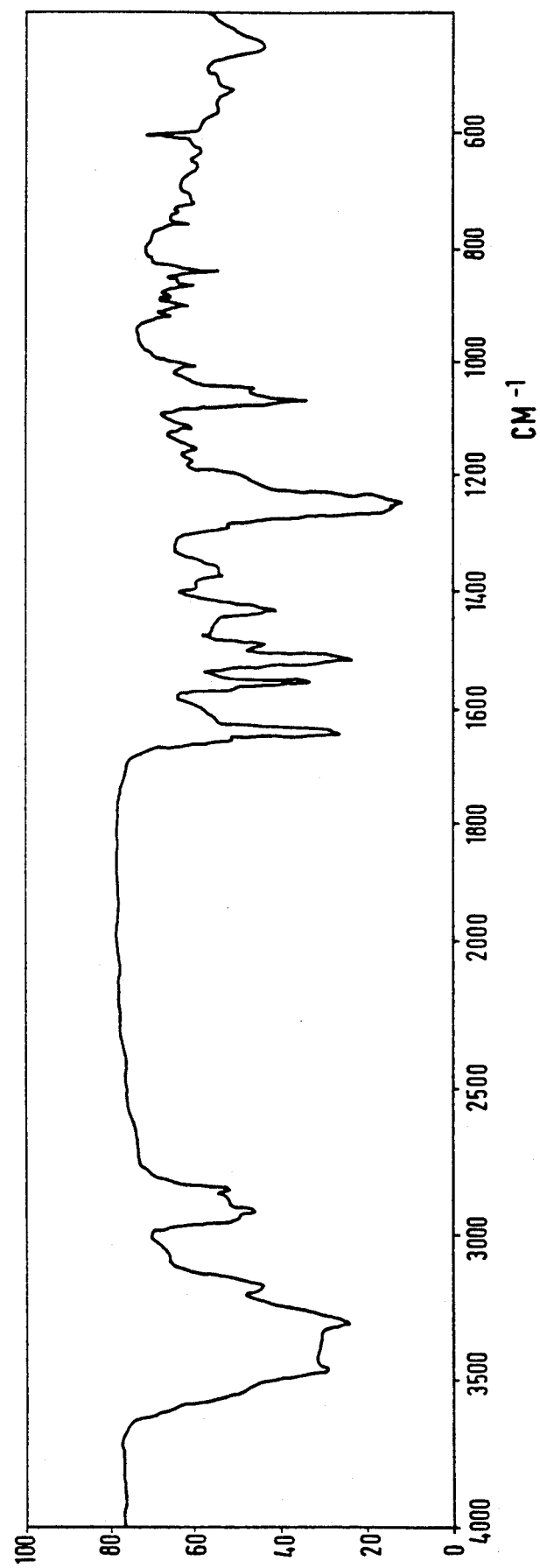
FIG. 8 shows the IR spectrum of 1-amino-4-di(2-hydroxyethylamino)-5-fluoro-2-nitrobenzene.

Yield: 4.2 g (32% of the theoretical value).
Melting point: 105° C.
IR spectrum: see FIG. 8.
$^1$H—NMR spectrum: (DMSO-$d_6$) $\delta = 2.9-3.2$ (4H, N—$CH_2$); $\delta = 3.3-3.7$ (4H, O—$CH_2$); $\delta = 4.3-4.6$ (2H, C—OH); $\delta = 6.6-6.8$ and 7.5-7.7 (2H, Ar—H); $\delta = 7.3$ (2H, $NH_2$).

Example 5

Preparation of 1-amino-5-fluoro-4(methyl-(2-hydroxyethyl))amino-2-nitrobenzene

Ethylene oxide is passed in portions into a mixture of 5.6 g (0.03 mol) of 1-amino-5-fluoro-4-methylamino-2-nitrobenzene, 50 ml of water and 30 g of monoethylene glycol dimethyl ether at 60° C. in the course of one hour and the reaction is monitored by thin layer chromatography. When the hydroxyethylation has ended, the monoethylene glycol dimethyl ether is distilled off, the mixture is cooled and the product which has precipitated is filtered off with suction. Recrystallization from toluene/2-butanol (7/3) gives 3.5 g of pure 1-amino-4-fluoro-4(methyl-(2-hydroxyethyl))amino-2-nitrobenzene.

Figure 5:
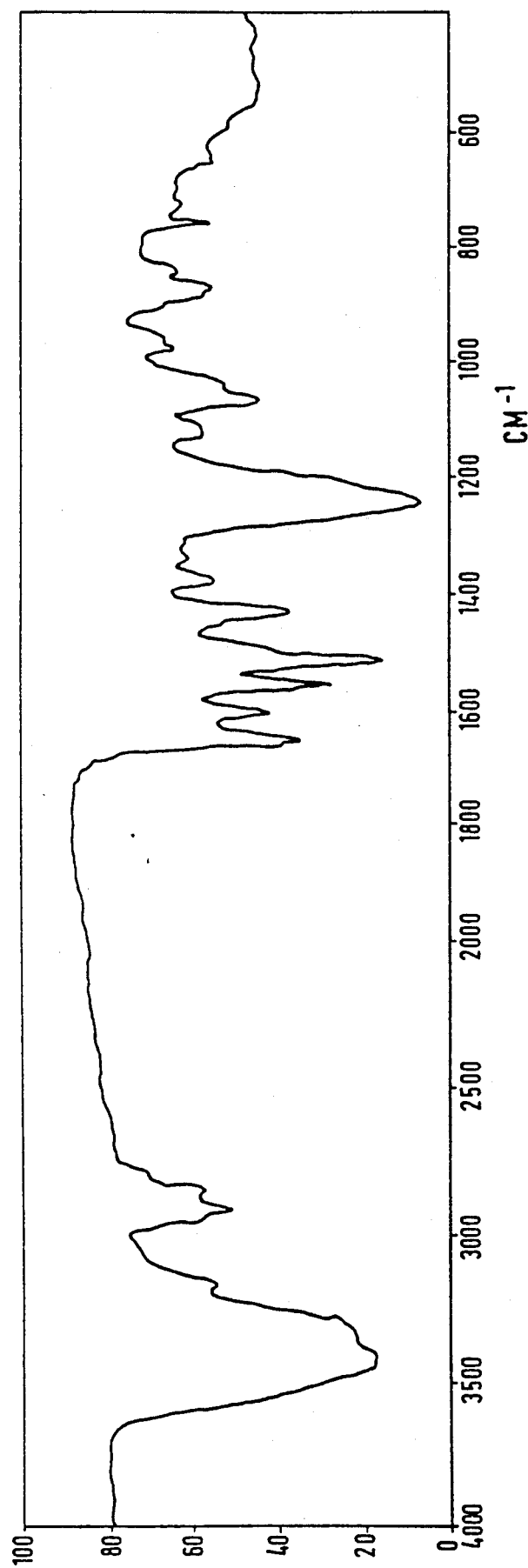
FIG. 5 shows the IR spectrum of 1-amino-5-fluoro-4-(methyl-(2-hydroxyethyl))amino-2-nitrobenzene.

Yield: 3.5 g (50% of the theoretical value).
Melting point: 97° C.
IR spectrum: see FIG. 5.
$^1$H—NMR spectrum: (DMSO-$d_6$) $\delta = 2.8$ (3H, $CH_3$—N); $\delta = 3.1$ (2H, $CH_2$—N); $\delta = 3.6$ (2H, $CH_2$—O); $\delta = 4.6$ (1H, O—H); $\delta = 6.8$ and 7.5 (1+1 H, Ar—H); $\delta = 7.4$ (2H, $NH_2$).

The dyestuffs of the general formula I are new and give hair colourations in pure red to purple colour shades of outstanding stability. Their preparation is described above.

The hair colouring agents according to the invention, which always contain at least one compound of the general formula I, are both those which are used without addition of an oxidizing agent and those for which addition of an oxidizing agent is necessary.

The former hair colouring agents without addition of oxidizing agent are those which also contain, in addition to the dyestuffs of the general formula I shown, other dyestuffs which are absorbed directly onto the hair. The following classes may be mentioned as examples of these dyestuffs known for colouring hair:

Aromatic nitro dyestuffs (for example 1,2-diamino-4-nitrobenzene), azo dyestuffs (for example C. I. Acid Brown 4, C. I. 14805), anthraquinone dyestuffs (for example C. I. Disperse Violet 4, C. I. 61105), and triphenylmethane dyestuffs (for example C. I. Basic Violet 1), it being possible for the dyestuffs of these classes to have an acid, nonionic or basic character, depending on the nature of their substituents.

Using these hair colouring agents which contain such mixtures of dyestuffs, fashionable blonde and brown shades of outstanding stability can also be achieved, in addition to pure fashion shades.

The formulation form of these hair colouring agents is preferably that of a liquid solution, possible solvents being water or mixtures of water and lower alcohols, such as, in particular, ethanol or isopropanol.

These liquid colouring agents should contain the dyestuffs of the formula shown in a concentration of about 0.01 to 1.0% by weight, preferably 0.05 to 0.5% by weight. The total content of dyestuffs lies within the limit of about 0.01 to 3.0% by weight.

The pH of these colouring agents lies in the range from 7 to 10.5, in particular pH 7.5 to 9.5, it being possible for the desired pH to be established chiefly with ammonia, but also with organic amines, such as, for example, monoethanolamine or triethanolamine. They are used in the customary manner by applying the agent to the hair, with which it remains in contact for a period of between 5 to 30 minutes. The hair is then rinsed with water, and if appropriate also with a weak organic acid, and dried. Weak organic acids which can be used are, for example, citric acid, tartaric acid and the like.

The hair colouring agents described above to which no oxidizing agent is added can also contain cosmetic polymers, via which setting of the hair is achieved at the same time as the colouring.

Examples which may be mentioned of the polymers known in cosmetics for this purpose are polyvinylpyrrolidone, polyvinylacetate, polyvinylalcohol or polyacryl compounds, such as acrylic acid polymers or methacrylic acid polymers, basic polymers of ester of these two acids and aminoalcohols and their salts or quaternization products, polyacrylonitrile and polyvinyllactams, and copolymers of such compounds, such as polyvinylpyrrolidone-vinylacetate and the like.

These agents contain polymers in the customary amount of about 1to 4% by weight. The pH of the agents lies in the range from 6.0 to 9.0.

The hair colouring agents with additional setting properties are used in the known and customary manner by fixing (placing) the hair in the style and then drying.

If appropriate, the hair colouring agents described above to which no oxidizing agent is added can contain other customary cosmetic additives, such as, for example, care substances, wetting agents, thickeners, softeners and perfume oils.

As mentioned above, the present invention also relates to those hair colouring agents with which the addition of an oxidizing agent is necessary. In addition to the dyestuffs according to the general formula I, they also additionally contain know oxidation dyestuffs which required oxidative development.

These oxidation dyestuffs are chiefly aromatic p-diamines and p-aminophenols, such as, for example, p-toluylenediamine, p-phenylenediamine, p-aminophenol and similar compounds which are combined with so-called modifiers, such as, for example, m-phenylenediamine, resorcinol, m-aminophenol and others, for the purpose of shading the colourations.

Such oxidation dyestuffs which are known and customary for hair colouring are described, inter alia, in the books by E. Sagarin, "Cosmetics", Science and Technology (1957). Interscience Publishers Inc., New York. pages 503 et seq; "Harry's Cosmeticology", 7th edition (1982), George Godwin, London, pages 521 and 547; C. R. Robbins, "Chemical and Physical Behavior of Human Hair", 2nd edition (1988), Springer Verlag New York Berlin Heidelberg London Paris Tokyo, pages 171 to 195.

In addition to pure fashion shades, fashionable blonde and brown shades can also be obtained with mixtures of these oxidation dyestuffs and the dyestuffs according to the general formula I.

These colouring agents to which oxidizing agents are added contain the dyestuffs according to the general formula I in a concentration of about 0.01 to 1.0% by weight, preferably 0.05 to 0.5% by weight. The total content of the dyestuffs in these colouring agents is about 0.1 to 5.0% by weight. The colouring agents are rendered alkaline, preferably to a pH of about 9.5 to 10.5, the pH being established in particular with ammonia. However, other organic amines, for example monoethanolamine or triethanolamine, can also be used for this purpose. Possible oxidizing agents for development of the hair colourations are chiefly hydrogen peroxide and addition compounds thereof. The physical form of these hair colouring agents is preferably that of a cream or a gel.

They are used in a known manner by mixing the hair colouring agents with the oxidizing agent before the treatment and applying the mixture to the hair.

After an action time of about 10 to 45 minutes, the hair is rinsed with water and if appropriate then with a weak organic acid, such as, for example, citric acid or tartaric acid, and dried.

The hair colouring agents with added oxidizing agent can contain known and customary cosmetic additives, such as, for example, antioxidants, complexing agents, thickeners, surfactants, care substances, perfume oils and others.

The examples below are intended to illustrate the subject matter of the application without limiting it thereto.

Example 6

Tinting agent 0.35 g of 1,4-diamino-5-fluoro-2-nitrobenzene
1.00 g of hydroxyethylcellulose
5.00 g of monoethanolamine lauryl sulphate
1.50 of myristyl alcohol
5.00 g of propylene glycol
87.15 g of water
100.00 g Light blonde natural hair is treated with the solution according to Example 6 at room temperature for 25 minutes and then rinsed with water and subsequently dried. The hair is tinted lustrous orange-red.

Example 7

Hair colouring cream 0.45 g of 1,4-diamino-5-fluoro-2-nitrobenzene
0.27 g of p-phenylenediamine-dihydrochloride
0.14 g of resorcinol 0.03 g of m-aminophenol
16.00 of cetyl alcohol
4.20 g of lauryl alcohol diglycol ether-sulphate, sodium salt
7.50 g of ammonia, 25% strength
0.20 g of sodium sulphite
71.21 g of water
100.00 g The colouring cream from Example 7 is mixed with equal parts of an aqueous 6% strength hydrogen peroxide solution, the mixture is applied to grey hair and after an action time of 30 minutes is rinsed out and the hair is subsequently shampooed and then dried.

The hair is coloured a lustrous copper-blonde.

Example 8

Hair setting agent 0.09 g of 1-amino-4-di(2-hydroxyethylamino)-5-fluoro-2-nitrobenzene
2.50 g of polyvinylpyrrolidine
0.11 g of glycerol
38.00 g of isopropyl alcohol
59.30 g of water
100.00 g Medium-blonde human hair is placed in position with the colouring setting solution from Example 8 and dried. The hair is coloured in a copper shade and set.

Example 9

Tinting agent 0.75 g of 1-amino-5-fluoro-4-methylamino-2-nitrobenzene
0.90 g of hydroxyethylcellulose
5.00 g of monoethanolamine lauryl sulphate
1.00 g of cetyl alcohol
5.00 g of ethyl diglycol
87.35 g of water
100.00 g Dark blonde natural hair is treated with the solution from Example 9 at 35° C. for 30 minutes and then rinsed with water and subsequently dried. The hair has been given an intensive lustrous Titian tint.

Example 10

Tinting agent 1.20 g of 1-amino-4-(2,3-dihydroxypropylamino)-5-fluoro-2-nitrobenzene
1.00 g of hydroxyethylcellulose
5.00 g of monoethanolamine lauryl sulphate
2.00 g of myristyl alcohol
5.00 g of benzyl alcohol
85.80 g of water
100.00 g Light brown natural hair is treated with the solution according to Example 10 at 40° C. for 30 minutes and then rinsed with water and subsequently dried. The hair has been given a lustrous red-brown colour shade.

Further variations and modifications of the invention will become apparent to those skilled in the art from the foregoing and are intended to be encompassed by the claims appended hereto.

German Priority Application P 39 17 114.0, filed on May 26, 1989, is relied on and incorporated by reference.

What is claimed is:

1. A compound of the formula I

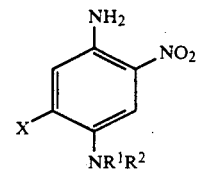

wherein $R^1$ and $R^2$ independently of one another each represent a hydrogen atom, a ($C_1$–$C_2$) alkyl group, or a hydroxy ($C_2$–$C_3$) alkyl group and X represents fluorine atom, with the proviso that when $R^1$ and $R^2$ is hydrogen then the other is not a hydroxy ($C_2$) alkyl group.

2. The compound according to claim 1 which is 1,4-diamino-5-fluoro-2-nitrobenzene.

3. The compound 1-amino-4-di(2-hydroxyethyl)amino-5-fluoro-2-nitrobenzene.

4. The compound according to claim 1 which is 1-amino-5-fluoro-4-methylamino-2-nitrobenzene.

5. The compound 1-amino-5-fluoro-4-(2-hydroxyethyl))amino-2-nitrobenzene.

6. An aqueous hair colouring composition for colouring keratin fibres which contain an effective amount of at least one compound of claim 1.

7. The composition according to claim 6, wherein said compound is present in an amount of from 0.001 to 5% by weight of the total composition.

8. The composition according to claim 6, further comprising at least one member selected from the group consisting of aromatic nitro dyestuffs, azo dyestuffs, anthraquinone dyestuffs, triphenylmethane dyestuffs, aromatic p-diamines dyestuffs and p-aminophenols dyestuffs.

9. The composition according to claim 6, wherein the pH of said composition lies in the range from approximately 2.5 to approximately 12.

10. The composition according to claim 6, further comprising at least one member selected from the group consisting of wetting agents, surface-active agents, emulsifiers, solubilizing agents, thickeners, softeners, perfume oils, antioxidants, complexing agents, and surfactants.

* * * * *